United States Patent [19]

Seale et al.

[11] 4,404,377
[45] Sep. 13, 1983

[54] HETEROCYCLIC/AROMATIC FLUOROCARBON SURFACTANTS

[75] Inventors: Virgil L. Seale, Houston, Tex.; James R. Stanford, Duncan, Okla.; James E. Briscoe, Duncan, Okla.; Glenn S. Penny, Duncan, Okla.

[73] Assignee: Nalco Chemical Company, Oak Brook, Ill.

[21] Appl. No.: 355,504

[22] Filed: Mar. 8, 1982

[51] Int. Cl.³ .............. C07C 95/02; C07C 95/08; C07D 295/08; C07C 43/13

[52] U.S. Cl. .................................. 544/87; 544/177; 546/102; 546/104; 546/139; 546/140; 546/180; 546/186; 546/240; 546/266; 546/344; 548/444; 548/518; 548/562; 568/615

[58] Field of Search ............ 544/87, 177; 546/102, 104, 139, 140, 180, 186, 240, 266, 344; 548/444, 518, 562; 564/285, 286, 294, 305, 442, 457, 462, 505; 568/615

[56] References Cited

U.S. PATENT DOCUMENTS

| | | | |
|---|---|---|---|
| 3,678,110 | 7/1972 | Boothe et al. | 568/615 |
| 3,681,413 | 8/1972 | Sweeney et al. | 568/615 |
| 3,681,441 | 8/1972 | Robertson | 568/615 |
| 3,742,013 | 6/1973 | Fielding | 564/285 |
| 3,758,593 | 9/1973 | Koshar | 564/285 |
| 3,882,182 | 5/1975 | Benninger et al. | 568/615 |
| 3,917,724 | 11/1975 | Martini | 568/615 |
| 3,952,060 | 4/1976 | Huber-Emden et al. | 564/285 |
| 3,984,357 | 10/1976 | Koshar | 564/285 |
| 4,000,175 | 12/1976 | Foulletier et al. | 568/615 |
| 4,014,926 | 3/1977 | Dear et al. | 568/615 |
| 4,059,629 | 11/1977 | Foulletier et al. | 568/615 |
| 4,085,137 | 4/1978 | Mitsch et al. | 564/286 |
| 4,165,338 | 8/1979 | Katsushima et al. | 564/285 |
| 4,168,277 | 9/1979 | Mitschke et al. | 568/615 |
| 4,209,456 | 6/1980 | Billenstein et al. | 260/458 R |
| 4,209,635 | 6/1980 | Ukihashi et al. | 568/615 |

FOREIGN PATENT DOCUMENTS 53-53608  5/1978  Japan.

*Primary Examiner*—Robert W. Ramsuer
*Attorney, Agent, or Firm*—John G. Premo; Robert A. Miller; Donald G. Epple

[57] ABSTRACT

Heterocyclic/aromatic fluorinated compounds of the formula

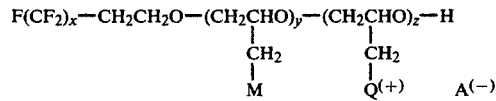

are disclosed. The cationic compounds are useful as surfactants.

6 Claims, No Drawings

HETEROCYCLIC/AROMATIC FLUOROCARBON SURFACTANTS

INTRODUCTION

The perfluoro moiety is useful in the synthesis of surface active compounds and agents. However, the perfluoro moiety is characterized as being both lipophobic, as well as hydrophobic. The perfluoro moiety can be found in substances that are of anionic character such as is described in U.S. Pat. No. 4,208,466 and can also be found in fluorine containing alkylsulfatobetaines as described in U.S. Pat. No. 4,209,456. In addition, the last referenced U.S. patent also describes cationic compounds containing functional groups which lead to a quaternary surfaces active compound containing both cationic charged nitrogen, as well as the perfluoro moiety.

The nitrogen based cationic perfluorinated compounds are dispersible in water and, therefore, are more readily applicable to a number of end uses. Proposed starting materials for preparing these cationic perfluoro amine compounds are the perfluoro substituted ethyl iodides represented by Formula I.

Formula I

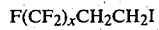

In the above Formula, x is an integer ranging from 2-12 or an integer representing an average value of from 6-8. However, when these perfluoroalkyl iodides are reacted with strong basic amines such as trimethyl amines, no quaternary perfluoro salts are obtained. The lack of formation of the desired quaternary perfluoro salts is caused by a dehydrohalogenation reaction which occurs when these iodo-fluorocarbons are exposed to strongly basic reaction conditions. The result of this dehydrohalogenation reaction yields almost exclusively perfluoro olefin.

Although U.S. Pat. No. 4,209,456 teaches the synthesis of cationic compounds containing perfluoro substitution attached to aromatic nitrogen compounds, the resultant products which are obtained do not have the kind of flexibility that one might desire when balancing both lipophobic, as well as hydrophobic character. It would, therefore, be an advance in the art if one were able to obtain perfluoro quaternary salts of heterocyclic and aromatic amines with greater flexibility in balancing hydrophobicity and hydrophilicity.

The present invention allows a variety of unique perfluoro cationic aromatic/heterocyclic amine compounds to be prepared in good yield without the occurrence of olefin formation and with excellent conversion of the expensive perfluoro precursor. The present invention further allows the balance of hydrophobicity and hydrophilicity by varying the ingredients and reactants used to prepare the finished compounds of this invention.

The present invention allows the synthesis of a variety of unique perfluoro cationic heterocyclic/aromatic amine compounds which have uses similar to those of commercial fluorocarbon surfactants. These compounds show utility in one or more of the following areas in which fluorocarbons are known to be effective:

(1) hydrocarbon emulsifiers in water;
(2) ore flotation aids;
(3) the treatment of porous substrates to modify surface characteristics (substrates such as leather, wood, porous plastics, and various natural or synthetic textiles may be treated);
(4) oil and water repellents;
(5) general surfactants;
(6) additives for dry powder fire extinguisher compositions;
(7) antimicrobials;
(8) soil repellents;
(9) additives for polishes and waxes;
(10) corrosion inhibitors for oils and lubricants;
(11) foaming and wetting agents;
(12) emulsifier and leveling agents for dye preparations.

THE INVENTION

The instant invention describes a perfluorohalogenated ether adduct (hereinafter the ADDUCT) which is easily reacted with heterocyclic and aromatic amines to yield very stable cationic heterocyclic-/aromatic perfluoro compounds having exceptional surface active characteristics. The compounds of the invention are represented by Formula II.

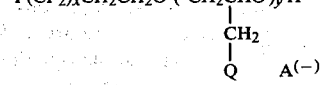

In the above Formula II, x is an integer of from 2-12 or an integer or fractional integer representing an average value of from 6-8. Also, y is an integer or fractional integer of from 1-20. Q represents a nitrogen containing heterocyclic or aromatic cationic radical. These nitrogen containing heterocyclic/aromatic cationic radicals are derived from the following chemical compounds: 2-H-pyrrole, pyrrole, imidazole, pyrazole, pyridine, pyrazine, pyrimidine, pyridazine, indolizine, isoindole, 3H-indole, indole, 1H-indazole, purine, 4H-quinolizine, quinoline, isoquinoline, phthalazine, naphthyridine, quinoxaline, quinazoline, 4aH-carbazole, carbazole, β-carboline, phenanthridine, acridine, phenanthroline, phenazine, imidazolidine, phenoxazine, cinnoline, pyrrolidine, pyrroline, imidazoline, piperidine, piperazine, indoline, isoindoline, quinuclidine, morpholine, azocine, azepine, 2H-azepine, 1,3,5-triazine, thiazole, pteridine, dihydroquinoline, hexa methylene imine, indazole, and any tertiary N-substituted alkyl derivatives thereof.

In the above Formula II, x is preferably an integer which has an average value from 6-8 and is most preferably representative of an average value equal to 8. The term "average value" indicates that the formula may represent an admixture of compounds which contain molecules in which x may be an integer from 2-12. In the meaning of average value, x may be an integer, such as 8, or a fractional integer, such as 7.5, 7.8, 8.5, and the like.

In the above formula, y is preferably an integer ranging between 1 and 4, with y most preferably being a fractional integer between 1.5 and 2.5. Q preferably represents a nitrogen containing heterocyclic or aromatic cationic radical obtained from the following compounds: pyridine, alkyl substituted pyridine, quinoline, isoquinoline, alkyl substituted quinoline, pyrazine, pyridazine, indolizine, naphthridine, quinoxaline, phthalizine, quinazoline, acridine, phenanthroline, quinuclidine, and azocine and the like. In addition, any N-substituted alkyl derivatives of pyrrole, imidazole, pyrazole, isoindole, carbazole, pyrrolidine, pyrroline, imidazolidine, indoline, isoindoline, morpholine, azepine, dihydroquinoline, hexa methylene imiine, indazole, and the like which would form quaternary salts when reacted with pendant halo groups derived from epihalohydrin are also preferred.

In addition, A in Formula II represents a halogen chosen from the group consisting of chlorine, bromine, or iodine which is present in its anion form. Q is most preferably chosen from the group consisting of pyridine, isoquinoline, quinoline, and N-methyl morpholine.

The compositions of this invention are prepared by a reaction of perfluoro alcohol with an epihalohydrin under anhydrous conditions. This reaction with the perfluoro alcohol is catalyzed by Lewis acid catalysts preferably chosen from the group consisting of antimony pentachloride, aluminum chloride, zinc chloride, ferrous or ferric chloride, boron trifluoride, and stannic chloride. Following the reaction of the perfluoro alcohol with epihalohydrin to form the ADDUCT, the halo group of the ADDUCT, which is originally found in the epihalohydrin molecule, is reacted with strong basic aromatic/heterocyclic amines under controlled conditions, thereby obtaining the perfluoro cationic heterocyclic compounds of the instant invention.

Q may also, in Formula II above, represent chloro, bromo, and iodo halogen radicals, up to about 50% of Q, i.e., Q may be chloro, bromo, iodo halogen radicals, as well as the cationic aromatic/heterocyclic amine radicals mentioned above, provided that no more than 50 mole percent of Q are halogen radicals of this type.

This alternative representation of Q in Formula II above covers ADDUCTS formed by sub-stoichiometric reaction with any of the heterocyclic/aromatic amines previously listed, but again most preferably pyridine, isoquinoline, quinoline, and N-methyl morpholine.

The instant invention describes a perfluorohalogenated ether ADDUCT which is easily reacted with heterocyclic and aromatic amines to yield very stable cationic heterocyclic/aromatic perfluoro compounds having exceptional surface active characteristics. In addition, the reactions and the starting materials used to form the compositions of this invention can yield admixtures of singular molecules which are advantageously used in various application areas which require these exceptional surface active characteristics. The compounds of the invention and the admixture compositions of the invention are represented by the formula:

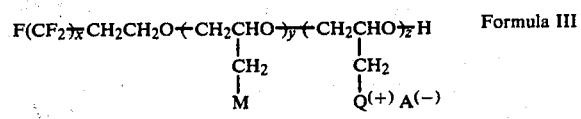

Formula III wherein x is an integer or a fractional integer representing average values from 2-12; y and z are integers or fractional integers representing average values from 0-20 provided that the sum (y+z) is from 1-20; M is a halogen raidcal; Q is a nitrogen containing heterocyclic/aromatic cationic radical, and A is a halogen anion.

The compositions of the invention are preferably those in which x in Formula III is an integer or fractional integer representing an average value from 6-8, y and z are integers or fractional integers representing average values from 0-5 provided that the sum (y+z) is from 1-5, Q is a nitrogen containing heterocyclic/aromatic cationic radical chosen from the groups previously mentioned but preferably from those radicals obtained by using the following compounds: pyridine, quinoline, isoquinoline, and N-methyl morpholine, A is the chloride anion, and M represents the chloro halogen radical.

The composition represented by Formula III is most preferred when x is from 6-8, y and z are from 0-2.5 provided that the sum of y+z is from 1.5-2.5, Q is a nitrogen containing heterocyclic/aromatic cationic radical obtained from pyridine, quinoline, isoquinoline, and N-methyl morpholine, and A and M are the chloride anion and chloro halogen radicals, respectively.

The Starting Perfluoro Compounds

The starting perfluoro compounds which are used to generate perfluoronated substituents within the compositions of this invention are derived from perfluoro substituted ethanols which are represented by Formula IV.

Formula IV

In the above Formula IV, x has the numeral values previously indicated in Formula II. A preferred perfluoro ethanol is commercially obtained from E. I. duPont de Nemours & Co. under the commercial name "Zonyl BA." This material is generally described by Formula IV, wherein x is equal to 6, 8, 10, 12 and wherein the average x is equal to 8. An average x again indicated that the compounds used may be an admixture of molecules, wherein x is individually 6, 8, 10, 12 with the numerical average being about 8.

The Epihalohydrins

The starting epihalohydrins used to react with the perfluoronated alcohols previously described are chosen from the group consisting of epichlorohydrin, epibromohydrin, and epiiodohydrin. The preferred epihalohydrin is epichlorohydrin.

The Aromatic and Heterocyclic Amines

The starting aromatic and heterocyclic amines used in the preparation of the quaternary and cationic ammonium salts of the invention are nitrogen containing aromatic/heterocyclics chosen from the group consisting of pyridine, quinoline, isoquinoline, alkyl substituted pyridines, alkyl substituted quinoline, 2-H-pyrrole, pyrrole, imidazole, pyrazole, pyrazine, pyrimidine, pyridazine, indolizine, isoindole, 3H-indole, indole, 1H-indazole, purine, 4H-quinolizine, phthalazine, naphthyridine, quinoxaline, quinazoline, 4aH-carbazole, carbazole, β-carboline, phenanthridine, acridine, phenanthroline, phenazine, imidazolidine, phenoxazine, cinnoline, pyrrolidine, pyrroline, imidazoline, piperidine, piperazine, indoline, isoindoline, quinuclidine, morpholine, azocine, azepine, 2H-azepine, 1,3,5-triazine, thiazole, pteridine, dihydroquinoline, hexa methylene imine, and indazoline. Other heterocyclic nitrogen containing compounds may also be used to obtain the perfluoro aromatic/heterocyclic cationic amine compounds of this invention. Any time a heterocyclic compound contains a secondary amine, N-alkylation of this secondary nitrogen would lead to compounds useful in the synthesis of the compositions of this invention. The most preferred aromatic/heterocyclic amines used to prepare the perfluoro cationic compounds of this invention are pyridine, isoquinoline, N-methyl morpholine, and quinoline.

The Catalysts

The catalysts used in the reaction between the perfluoro alcohols previously described and the epihalohydrins described above are chosen from Lewis acid materials. These catalysts are represented by antimony pentachloride, boron trichloride, boron trifluoride, stannic chloride, ferric and ferrous chloride, as well as the Lewis acid compounds previously mentioned. The Lewis acid preferred is antimony pentachloride, used either as an etherate compund or as pure anhydrous material. The catalyst is used at a concentration ranging from 0.1% based on the final ADDUCT up to about 1.0% by weight based on the final ADDUCT weight. A preferred range of catalyst is between 0.1% and 0.5% by weight based on the final ADDUCT. A most preferred catalyst concentration, particularly in reference to the use of antimony pentachloride, is between 0.2 and 0.3% by weight of the final ADDUCT obtained in this reaction.

It has been found that basic catalysts such as potassium hydroxide, sodium hydroxide, and sodium methoxide do not yield the final ADDUCT of this instant invention when used to react the perfluoro alcohols, described above, with the epihalohydrins also previously mentioned.

Reaction Conditions, Synthesis of Perfluoro Aromatic/Heterocyclic Amine Compounds and Quaternary Salts The compounds of the invention are made using a two-step synthetic technique. The first reaction comprises the reaction of a perfluoro ethanol, preferably the Zonyl BA perfluoroethanol material, with an epihalohydrin under the catalytic conditions previously described. After this ADDUCT product is produced, it is then reacted with the heterocyclic/aromatic amines described above to produce the finished nitrogen containing perfluoro compounds of this invention.

The reaction of the perfluoro alcohol with epichlorohydrin is accomplished by using one of two methods set forth below. The description uses epichlorohydrin as the epihalohydrin.

Method 1

To an autoclave which has previously been charged with the perfluoro alcohol and catalyst, an amount of epichlorohydrin is added at such a rate, so as to maintain a reaction temperature between 60° and 100° C. The reaction is catalyzed by a Lewis acid, preferably antimony pentachloride, and additional catalyst may be added simultaneously with the addition of epichlorohydrin. Epichlorohydrin may be used in higher molar quantities, such that the molar ratio of perfluoro alcohol to epichlorohydrin will vary between 1:1 and 1:5 in the final ADDUCT. The preferred amount of epichlorohydrin is approximately 1.5 moles of epichlorohydrin charged to the autoclave per mole of perfluoro alcohol originally charged to the autoclave. The purpose of the 50% molar excess of epichlorohydrin is to obtain essentially complete reaction of the expensive perfluoro alcohol starting compounds. An equal molar ADDUCT may, however, be synthesized and is to be considered included in this teaching.

Once the epichlorohydrin is charged to the autoclave in its entirety, the autoclave is maintained at a temperature of at least 100° C. at the concurrent pressures which are normally obtained from the reactants and initial charging conditions for at least 30 minutes. The reaction is followed to completion by monitoring unreacted epichlorohydrin via Gas Chromatographic techniques. The autoclave may be cooled and samples removed as soon as residual epichlorohydrin is determined to be about 0.2 weight percent or below. Additional epichlorohydrin may be charged to obtain higher mole ratios of epichlorohydrin and perfluoro alcohol.

Alternatively, the heterocyclic/aromatic amine compound which is chosen to react with the formed ADDUCT may be added to the autoclave and the cationic amine formation reaction commenced. All of the above reactions are anhydrous in nature and are accomplished in an inert atmosphere such as is obtained by a nitrogen environment. The cationic amine reaction is not required to be anhydrous in nature. In fact, slight improvements in the product yields are obtained when water, methanol, ethanol, and other lower molecular weight alcohols, and mixtures of water with these lower molecular weight alcohols are present. The preferred method of amine reactions or quaternization of the ADDUCTS mentioned above include the addition of water, alcohol, or mixtures thereof.

Method 2

Uses a round-bottomed flask equipped with a condenser, stirrer, dropping funnel, and nitrogen bleed, to which is added the desired quantity of the perfluoro alcohol. The Lewis acid catalyst is added after nitrogen sparging of the perfluoro alcohol to achieve anhydrous condition. The preferred catalyst is again antimony pentachloride. Epichlorohydrin is added at such a rate to obtain and maintain a reaction temperature ranging between 60° and 100° C.

After addition of epichlorohydrin is complete, the reactants are heated for at least an additional 30 minutes at a temperature of about 100° C. As before, additional epichlorohydrin may be added, so as to increase the mole ratio of the ADDUCT obtained. When the preferred ADDUCT is obtained, the cationization reaction may be connected in the same flask by adding the appropriate heterocyclic/aromatic amine.

The reaction between the epichlorohydrin/perfluoro alcohol ADDUCT and the appropriate amine may be conducted using either one of two methods

1. Cationization Method I

To the autoclave containing the perfluoro alcohol-epichlorohydrin ADDUCT (derived from Method 1 above) is added sufficient heterocyclic/aromatic amine to react with the chloro functionality of the ADDUCT. This reaction may be followed to completion by ionic chloride analysis. Enough methanol may be added to the autoclave so as to dilute the reactants to approximately 50 weight percent. The reactants then are heated under pressure to temperatures not exceeding 120° C. until the cationization reaction is essentially completed. The autoclave is cooled and the product is removed from the autoclave as the methanol solution. The product may be diluted to desired concentrations by either the addition of methanol or water.

2. Cationization Method II

The perfluoro alcohol/epichlorohydrin ADDUCT generated from Method II above is added to a closed vessel along with sufficient heterocyclic/aromatic amine to react with the chloro functionality of the epochlorohydrin ADDUCT. Sufficient methanol is added to dilute the reactants to approximately 50 percent by weight. The closed vessel is heated in an oven to temperatures not exceeding 120° C. until cationization is essentially completed.

To better describe and exemplify the invention, the following examples are set forth:

EXAMPLE 1

Into a three-necked, round-bottomed flask equipped with stirrer, condenser, and pressure equalized addition funnel, was placed 232 grams (½ mole) of the duPont Zonyl BA perfluoro alcohol. A slow nitrogen purge created a nitrogen atmosphere within the flask which was maintained throughout the reaction. The flask contents were heated to 70° C. and 1 milliliter of BF₃ etherate was added. While stirring, 62 grams (approximately ⅔ moles) of epichlorohydrin was added to the flask in a drop-wise fashion. The reaction exotherm was kept below 95° C. by adjusting and controlling the addition rate of epichlorohydrin. The reaction mixture continued to exotherm throughout the addition of epichlorohydrin.

After the epichlorohydrin addition was completed, the reactants were heated to approximately 110° C. and maintained at that temperature for approximately 1 hour. The flask contents were cooled to 70° C. and then the quaternization reaction was begun.

The quaternization reaction is obtained by transferring the flask contents to a pressure vessel and adding sufficient quantities of pyridine to quaternize all of the chloro groups contained in the synthesized epichlorohydrin/perfluoro alcohol ADDUCT. An additional 10 grams of pyridine were added to the flask to guarantee complete quaternization. During the quaternization step, the flask was closed to the atmosphere, under pressure, and heated to temperatures of approximately 120° C. After quaternization was complete, the flask contents were cooled, the flask vented to the atmosphere, and the contents removed from the flask and diluted to desired concentrations by the addition of either methanol or water solvent.

EXAMPLE 2

In a three-necked, round-bottomed flask equipped with a stirrer, condenser, and pressure equalized dropping funnel, along with means to maintain a nitrogen purge, was placed 500 grams of the duPont Zonyl BA perfluoro alcohol. A slight nitrogen purge was initiated and maintained through the reaction. The perfluoro alcohol was warmed to approximately 60° C. and 1 milliliter of BF₃ etherate was added.

Approximately 270 grams of epichlorohydrin was added slowly to this reaction flask while it was stirred. The temperature rose gradually to 90°–95° C. but was generally kept below 85° C. After addition of epichlorohydrin was completed, the temperature of the reaction flask and its contents was raised to about 110° C. and maintained at that temperature for approximately 1 hour. The product obtained from this reaction was cooled and removed from the reactor.

This procedure was followed repetitively to synthesize the starting material needed to complete the several subsequent reactions with various aromatic/heterocyclic amine reactants.

EXAMPLE 3

Two hundred grams of epichlorohydrin/perfluoro alcohol ADDUCT obtained from Example 2 was charged to a PARR autoclave. To this same autoclave, 64 grams of pyridine and 264 grams of methanol were also charged. The autoclave was closed to the atmosphere and the contents heated to approximately 120° C. for about 2 hours. The pressure within the autoclave rose to approximately 160 pounds per square inch and then dropped to about 140 pounds per square inch, as the quaternization reaction proceeded. The reactor was then cooled, the product was neutralized with HCl, and the solution of the perfluoro aromatic quaternary ammonium complex was removed.

EXAMPLE 4

Two hundred fifty-two grams of the ADDUCT formed by the reaction outlined in Example 2 was placed in an autoclave with 122 grams of quinoline and 374 grams of methanol. The autoclave vessel was closed and heated to 120° C. for about 2 hours. Pressure rose to about 160 pounds per square inch but dropped to about 140 pounds per square inch at the end of the reaction time. The autoclave reactor was cooled, the product solution neutralized with HCl, and the solution stored for further testing.

EXAMPLE 5

Two hundred fifty-two grams of the ADDUCT formed by the reaction outlined in Example 2 is placed in an autoclave with approximately 75 grams of quinoline and 375 grams of methanol. The autoclave vessel is closed and heated to 120° C. for about 2 hours. Again, pressure rises in the autoclave but drops towards the end of the reaction. The autoclave reactor is cooled and the product solution, which contained a partially quaternized ADDUCT was stored for further testing.

EXAMPLE 6

Approximately one-tenth of a mole of the ADDUCT formed by the reaction outlined in Exaple 2 may be placed in an autoclave along with about 0.11 moles of piperidine. Sufficient methanol may be added to this mixture to obtain a 50 weight percent solution of the anticipated final amine hydrochloride salt. The autoclave should be closed to the atmosphere and heated to approximately 120° C. for no more than 6 hours. Autoclave pressure would be expected to increase slightly but should drop towards the end of this reaction. After the reaction is complete, the autoclave reactor should be cooled and the product solution neutralized with additional hydrochloric acid. The methanol/water solution will contain a piperidine hydrochloride salt of the ADDUCT in solution.

EXAMPLE 7

Approximately 0.5 moles of the ADDUCT formed in Example 2 should be charged to a round-bottomed flask equipped with a condenser, a stirrer, a thermometer, and reactant addition pressure equalized dropping funnel. Sufficient methanol should be added so as to obtain a 50 weight percent solution of the anticipated product. The round-bottomed flask should be heated to reflux temperatures which will closely correspond to the boiling point of methanol. After reflux has been established, 0.55 moles of N-methyl morpholine is slowly added to the flask contents using the pressure equalized dropping funnel. Cationization reaction is complete within 6 hours. The contents of the vessel are cooled and moved to an autoclave which is closed to the atmosphere, blanketed with nitrogen, and heated to 120° C. for an additional 2 hours. This final reaction time is sufficient to complete the quaternization of Example 2 ADDUCT and to obtain a quaternary salt derived from N-methyl morpholine. This quaternized ADDUCT is then stored for further testing.

Having described my invention, we claim:

1. A composition represented by the formula:

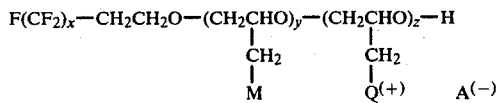

wherein x is an integer or a fractional integer representing average values from 2–12; y and z are integers or fractional integers representing average values from 0–20 provided that the sum (y+z) is from 1–20; M is a halogen radical; Q is a nitrogen containing heterocyclic/aromatic cationic radical, and A is a halogen anion.

2. The composition of claim 1 wherein x is an integer or fractional integer representing an average value from 6–8; y and z are integers or fractional integers representing average values from 0–5 provided that the sum (y+z) is from 1–5; Q is a nitrogen containing heterocyclic/aromatic cationic radical chosen from pyridine, quinoline, isoquinoline, and N-methyl morpholine radicals, and A and M are the chloride anion and chloro radical.

3. The composition of claim 1 wherein x is from 6–8, y and z are from 0–2.5 provided that the sum (y+z) is from 1.5–2.5; Q is a nitrogen containing cationic radical chosen from pyridine, quinoline, isoquinoline radicals, and A and M are the chloride anion and chloro halogen radical, respectively.

4. A composition represented by the formula:

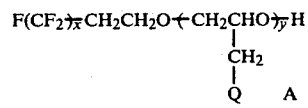

wherein x is an integer of from 2–12; y is an integer or fractional integer representing an average value of from 1–20, Q is a nitrogen containing heterocyclic/aromatic cationic radical, and A is a halogen anion.

5. The composition of claim 4 wherein x is an integer having an average value from 6–8, y is an integer or fractional integer between 1–4, Q is a nitrogen containing aromatic cationic radical, and A is chosen from chloride, bromide, and iodide anions.

6. The composition of claim 4 wherein x is from 6–8, y is from 1.5–2.5, Q is a nitrogen containing cationic radical formed from pyridine, quinoline, isoquinoline, and N-methyl morpholine, and A is the chloride anion.

* * * * *